United States Patent [19]

Medeiros et al.

[11] Patent Number: 5,831,859
[45] Date of Patent: Nov. 3, 1998

[54] PHARMACEUTICAL RECORDKEEPING SYSTEM WITH LABELLING FOR MANUFACTURING RAW MATERIALS

[75] Inventors: Joel E. Medeiros, Delran; Louis M. Gaburo, Madison; Stewart E. Hartkopf, Cherry Hill, all of N.J.; Harvey Cohen, Huntingdon Valley, Pa.

[73] Assignee: Base Ten Systems, Inc., Trenton, N.J.

[21] Appl. No.: 448,929

[22] Filed: May 25, 1995

Related U.S. Application Data

[63] Continuation-in-part of Ser. No. 109,788, Aug. 20, 1993, abandoned.

[51] Int. Cl.$^6$ .................................................. G06F 17/60
[52] U.S. Cl. .................. 364/478.06; 235/325; 235/385; 364/468.13; 364/468.22; 364/468.23; 364/478.03; 364/478.1; 364/478.13; 364/478.14; 371/53; 371/54
[58] Field of Search .............................. 364/403, 468.22, 364/468.23, 478.13, 478.03, 468.13, 478.1; 371/53, 54; 235/375, 385

[56] References Cited

U.S. PATENT DOCUMENTS

| | | | |
|---|---|---|---|
| 4,680,456 | 7/1987 | Drexler | 235/454 |
| 4,857,716 | 8/1989 | Gombrich et al. | 235/462 |
| 5,161,163 | 11/1992 | Bossen et al. | 371/54 |
| 5,166,884 | 11/1992 | Maney et al. | |
| 5,222,855 | 6/1993 | Bernard, II et al. | 414/331 |

*Primary Examiner*—Gail O. Hayes
*Assistant Examiner*—William N. Hughet
*Attorney, Agent, or Firm*—Sprung Kramer Schaefer & Briscoe

[57] ABSTRACT

A system for recordkeeping, comprising assigning a bar code label to material to be processed including information identifying the material and successively moving the material into a plurality of processing stations. At each station the bar code label is read, a second bar code label including information relating to a processing operation is assigned to the material, the second bar code label is read, a processing operation is performed in accordance with the second bar code label and a third bar code label is assigned to the material including information corresponding to results of the processing operation. The information from the first, second and third labels are stored in a main storage device.

7 Claims, 6 Drawing Sheets

PHARMACEUTICAL RECORDKEEPING SYSTEM WITH LABELLING FOR MANUFACTURING RAW MATERIALS

This application is a continuation-in-part application of U.S. application Ser. No. 08/109,788, filed on Aug. 20, 1993 and now abandoned.

BACKGROUND OF THE INVENTION

The present invention relates to a system for assuring compliance with procedures in ongoing production processes and in particular a pharmaceutical recordkeeping system.

Currently, many manufacturing processes are regulated by government and state agencies which set forth procedures with which manufacturers must comply in order to obtain regulatory approval for their products. For example, pharmaceutical manufacturing processes must comply with NDA/ANDA procedures and must accumulate permanent raw material and manufacturing batch processing records in compliance with FDA regulations.

While manufacturers have complied with these rules and regulations by manual recordkeeping, there has been a need for an automated system which can adapt to the specific needs of each manufacturer while maintaining compliance with manufacturing procedures and recordkeeping requirements.

SUMMARY OF THE INVENTION

The main object of the present invention is to provide an automated system for assuring compliance and permanent records of ongoing production processes.

Another object of the present invention is to improve productivity by reducing paperwork, automating data acquisition, improving materials flow and by authorizing operators under controlled and secure access conditions.

The system according to the present invention can be implemented into a batch processing oriented manufacturing operation for pharmaceutical manufacturing, bulk pharmaceutical chemical formulation, food and beverage processing, consumer package goods manufacture, clinical laboratory diagnostics reagent production and medical device manufacturing.

In accordance with the invention, data can be input via keyboard and mouse, touch screens, keypad data entry, wireless and plug-in bar code scanners and terminals and the like.

One feature of the present invention is the use of an electronic signature to control employee security access. Each operator is identified to the system by a name code or bar code and a password. The combination of either the name code and password or the bar code and password represents the electronic signature of the operator.

In accordance with the method of the present invention, sample inspections and tests insure that only those materials and product batches which meet quality standards are processed into finished product and shipped to customers. The method automatically requests the necessary samples, inspections and tests and maintains the status of the results in a database. The system will only allow those materials and product batches which have met these criteria to be processed further.

All data associated with a particular product batch, including all materials used in the process, are automatically assembled into a complete batch record for review prior to product distribution. The records may be reviewed in their completed state or in the sequence that the data and verification were recorded.

The system also utilizes redundant storage of records to insure data integrity. For example, during the performance of a blending step in the manufacturing process of a particular product, a sequential logging file would record the identification of the performing operator, the batch record file and the facility and equipment file with every operation time and date stamped. The data would be recorded in a redundant server as each step was completed to prevent data loss should a piece of workstation hardware fail.

Furthermore, each data entry in the system generates a unique check code. The check code permanently binds an electronic signature to the event. As part of the system, background programs check the recorded data and the check codes and these check codes not only verify that the data stored and retrieved is identical, but it also looks for inconsistent or unauthorized modifications of the records. Should a discrepancy be detected, it will be reported to a system manager.

All data recorded in the system can be archived on unalterable compact disk write-once read-many media. The timing of the periodic archiving is controlled by the system and types of data to be archived include sequential event logging, completed material lot histories, completed batch records and document revision histories.

Under the control of the system, certain operators can be limited to using one particular workstation. Each significant event performed on the system is recorded in the database with a date and time stamp and the identification electronic signature of the individual performing the event.

The present invention makes full use of bar coded labels, with comprehensive tracking and verification of materials from receipt, through inprocessed batches, to packaged product and shipping. Movements and status are monitored in accordance with the present invention and controlled. Unique material lot numbers are generated and bar coded labels are printed to identify each container. Prompts and bar coded labels are provided for material sampling, sample inspections and tests in quality control review accepts or rejects material and the location of material is established with bar coded warehouse rack and aisle designations.

Unique batch numbers are generated on bar code labels and withdrawal and dispensing of materials are prompted in accordance with released batch production control records. Materials are automatically allocated to each batch on a first-in/first-out basis or by specific allocation through management intervention. Prompts and bar coded labels provide for dispense material and batch identification, with automatic material inventory level update. There is automatic reconciliation of material lot weight or measures after depletion and bar coded labels are generated for all inprocess product and sample containers.

The scanning of container bar code labels provides the system of the present invention with the ability to track and verify the materials and batches by their lot and batch numbers. The system alerts operators if they attempt to move or use materials incorrectly. Wireless or plug-in palm top bar code scanners and terminals allow this verification to be implemented in larger areas, such as a warehouse, and the reconciliation of material lot total weights and measures with specific attention to product labels and printed containers is performed by the system.

The system also handles material dispensing and recipe tracking. Material is delivered to local inventory and, after reading or generating the bar coded data describing the materials, the dispensing process is initiated. The system acts to insure that equipment, room, personnel and container rules are observed. As each step is undertaken, the system can verify that the recipe and its constraints are not violated.

The system verifies that material delivered to local inventory with potency data is in accordance with the equation relating weight or volume to potency. The system can alert the operator if materials do not meet required tolerances or if dispensed material does not fall within the allowed weight ranges. The system can provide multiple dispensing of a single ingredient for a single batch where the ingredient is mixed in different stages.

The system identifies dispensed ingredients and quality control samples when required with bar codes and specifies quarantine or acceptance. Material to be returned to the warehouse, local inventory, special storage, waste or which has outlived its shelf life is routed as required.

The system can only proceed once prescribed data, personnel identification or electronic signature entries, as defined by management have been made at the time of completion of a process step. Alerts can be provided by the system when incorrect responses are received, with the option to require a second party intervention to correct an entry. Thus the system insures data integrity and compliance with defined procedures.

These and other objects of the present invention are also achieved in accordance with the present invention by the use of a system comprising portable memory devices (PMD's) and associated stations having read/write equipment to document process requirements and permanently record process data, all under the control of a main processor. The PMD's are secure, serialized, non-alterable electronic tags which travel with the materials or manufacturing batches. Data is permanently written into the "write once read many" memory in the PMD. An example of a device which is useful for this purpose is the Fujitsu MB98A6070, MB98A6080, MB98A6090 and MB98A6100 one time programmable read only memory card. Once data has been written into the PMD, the data cannot be altered, but, can be read as many times as necessary thereafter. Additional data can be sequentially added to the PMD, up to the memory capacity of the PMD.

In accordance with the invention, master production and control procedures and requirements are entered into a PMD when manufacturing is initiated. The identification and process record data required by the FDA, is written into the PMD's on a real time basis for comparison with the process requirements and the permanent archiving of actual process data. The data is written into and retrieved from the PMD's using stationary or handheld read/write equipment at each process station. There are two different types of PMD's available. One type uses a radio frequency or electromagnetic signal to communicate with the PMD during the read/write functions. The other type of PMD plugs directly into the read/write equipment, making a direct electrical connection for communications. Management of the recorded data is controlled by a main processor linked to each station by a bus or network connection. The main processor controls the security and accessibility to the data in each PMD, performs data comparisons for verification of materials, products, equipment, test samples and controlled parameters contained within each PMD to provide alerts in the event of errors. The main processor provides an index of the PMD's and can also assemble and format a printout of the stored data for review and evaluation at a later time.

In a particularly advantageous commercial embodiment of the present invention, a pharmaceutical manufacturing system can be implemented wherein individual PMD's are assigned to each lot of raw material upon receipt by the manufacturer. The specific material identification, receipt date, weight or measure, unique lot number and a delineation of all sample test requirements for final acceptance are written into the PMD for each lot. When samples are withdrawn from the material lot for acceptance tests, intermediary PMD's are assigned to each sample to assure correlation of the samples to the material in quarantine. The specific material identification and test requirements are read from the raw material PMD and written into the sample PMD. The sample PMD then travels with the sample of material through the completion of the testing. Test pass or fail notations are written into the sample PMD by the test laboratory at the specific station and the sample PMD is returned to the raw material quarantine area for correlation with the original material PMD through a dual read and compare routine. Following this routine, the test results are read from the sample PMD and written into the correct raw material PMD. The sample PMD can then be reused for the sampling of other raw material, or archived when the memory capacity has been exhausted.

When all material acceptance requirements have been satisfied, the raw material PMD is again written into to indicate that the material is accepted and the raw material, together with its raw material PMD, is moved together out of quarantine and into usable stock.

The system is also used in the dispensing of raw materials for the manufacturing processes. Manufacturing components are requested from the raw material in usable stock via a PMD containing the identification of the manufacturing batch and the specifics of the requested raw material. The application of a dual read and compare routine to the requesting manufacturing component PMD and the raw material PMD assures positive correlation between the requested material and the actual material that is dispensed.

The specific manufacturing batch identification and dispensed weight or measure are written into the raw material PMD each time material is dispensed or issued. Likewise, the raw material lot identification and dispensed weight or measure are written into the manufacturing component PMD for return to the manufacturing process along with the dispensed material.

Other information is added to the PMD's at various times during the process and annotations of the date and time, the identification of the performing and verifying individuals and traceable references to any problem investigations, represent some of the additional data included in the PMD.

When the lot of raw material has been exhausted, reconciliation of the dispensed versus the total received weight or measure may be performed since the raw material PMD contains a complete and unalterable history of the specific lot of raw material. The raw material PMD is then archived for later retrieval of data for the duration of the required FDA retention period. If sufficient unused memory capacity remains, the PMD may be used for additional lots of raw material before being retired to the archives.

In manufacturing, two PMD's are assigned to each manufacturing batch at the time of production authorization. One PMD, the manufacturing PMD, is formatted with the specific product and batch identification, along with a reproduction of the complete master process and control requirements for the product. The second PMD, the component PMD, is formatted with some of the same information, however, with specific annotations with all of the material components required during the manufacturing process.

As the manufacturing process is implemented, actual process information is recording on the manufacturing PMD. This information includes the equipment used, the yields obtained and compliance with specific process limitations such as time, temperature and speed. Comparison routines verify the actual data with the established master production and control requirements or limits and can alert the operator to the need to resolve any discrepancies.

As described with regard to the raw material, intermediary samples PMD's can be used for the manufacturing in process sample tests. The sampling requirements are written from the manufacturing PMD into the sample PMD when the sample is required. Later, the results of the sample testing are written from the sample PMD into the manufacturing PMD upon successful completion of each test.

The associated component PMD is used and actually moves between the manufacturing process and the stock room, to verify the dispensing of the required material. As with the correlation of the requested and dispensed raw material heretofore described, the component PMD also provides positive assurance that the correct material is used in the manufacturing process. The dual read and compare routine is applied to both the component and manufacturing PMD's upon return of the dispensed material from the stock room and before introduction of the raw material into the manufacturing process.

Other required information can also be added to the manufacturing and component PMD's at various times during the process, including verifications to proceed and final acceptance of the product by quality assurance.

Assuming bulk product is completed and held for later packaging, two new PMD's are assigned to each packaging lot. These PMD's are used in the same manner as the manufacturing and component PMD's to control and monitor the packaging process and materials. Product distribution may be added to the packaging PMD as the product is shipped.

The bulk manufacturing and packaging PMD's contain a complete unalterable history of the process, including verification of compliance with the requirements of the master production and control record. These PMD's are then archived after depletion of the batch of bulk production and completion of finished product inspections, record reviews and distribution of the packaged products for FDA record review in the future. If sufficient unused memory capacity remains, the manufacturing and packaging PMD's may be used for additional batches before being retired to the archives.

Each PMD contains a unique, permanently recorded, serial number in the memory. The additional permanently recorded cross referencing of material lot numbers, manufacturing batch numbers, and the PMD serial numbers in companion PMD's, make it virtually impossible to covertly alter or destroy actual recorded historical data. Therefore, the invention prevents undetected data tampering and an extremely high level of archive data security.

Throughout the raw material and manufacturing processing, the PMD data is periodically accessed and stored in a database in the main processor for appropriate analysis. A cross referenced index of the PMD's is established, updated, and maintained in the database of the main processor to facilitate the location of specific archived material or product batch data.

DETAILED DESCRIPTION OF THE INVENTION

Figure 1:
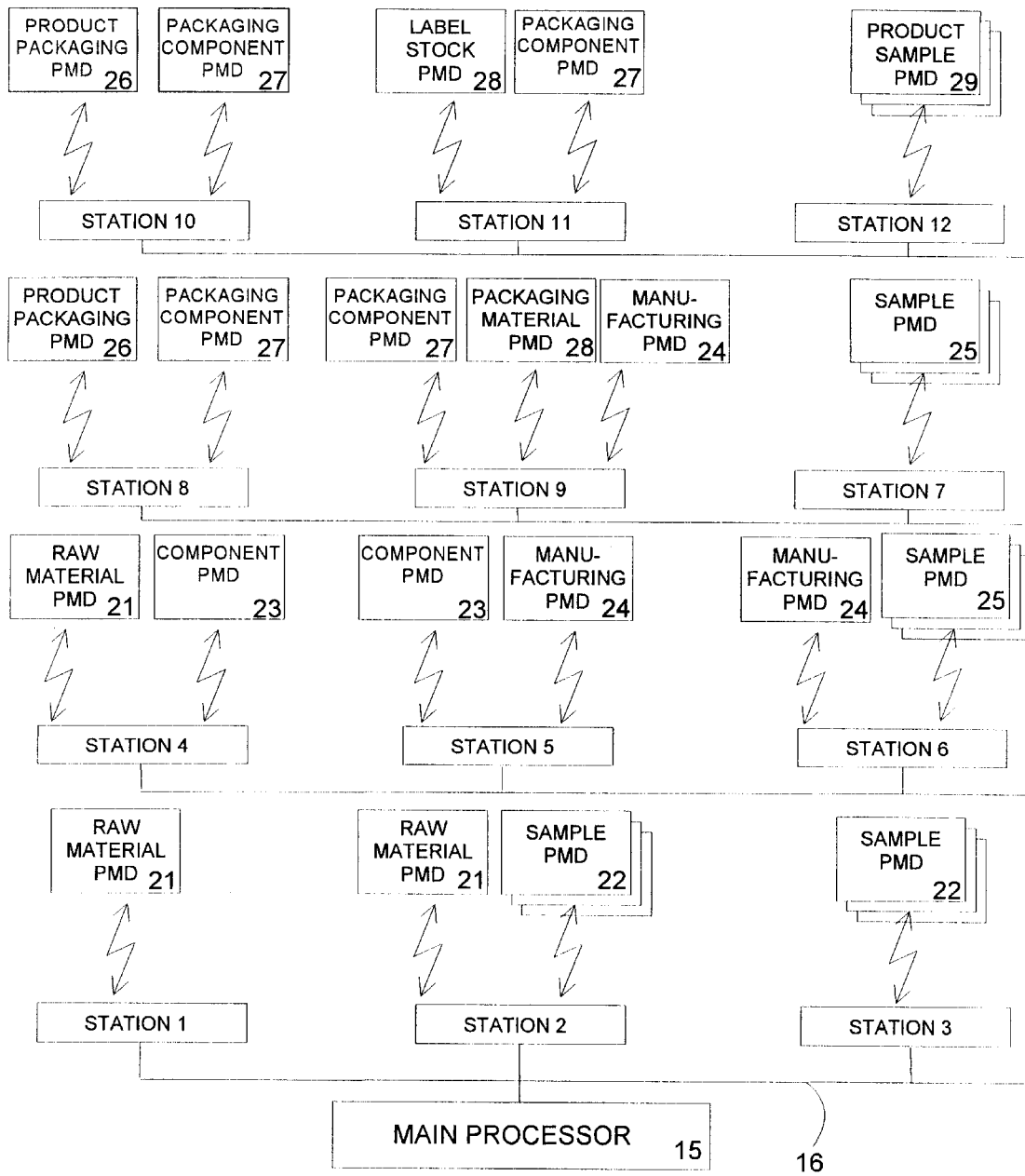
FIG. 1 is a block diagram of the system according to the present invention.
Figure 2:
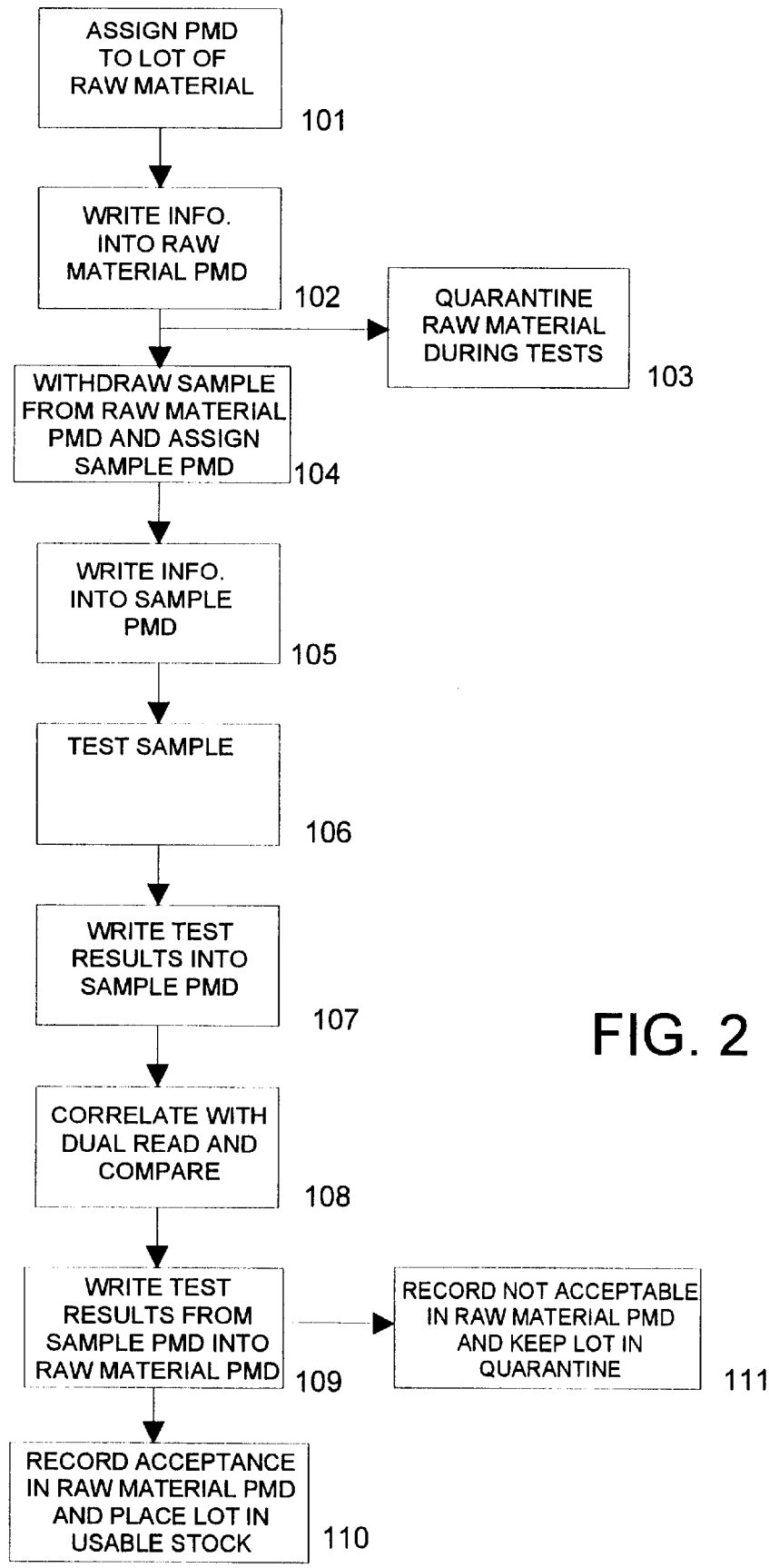
FIG. 2 is a flow chart of a method in accordance with the present invention.
Figure 3:
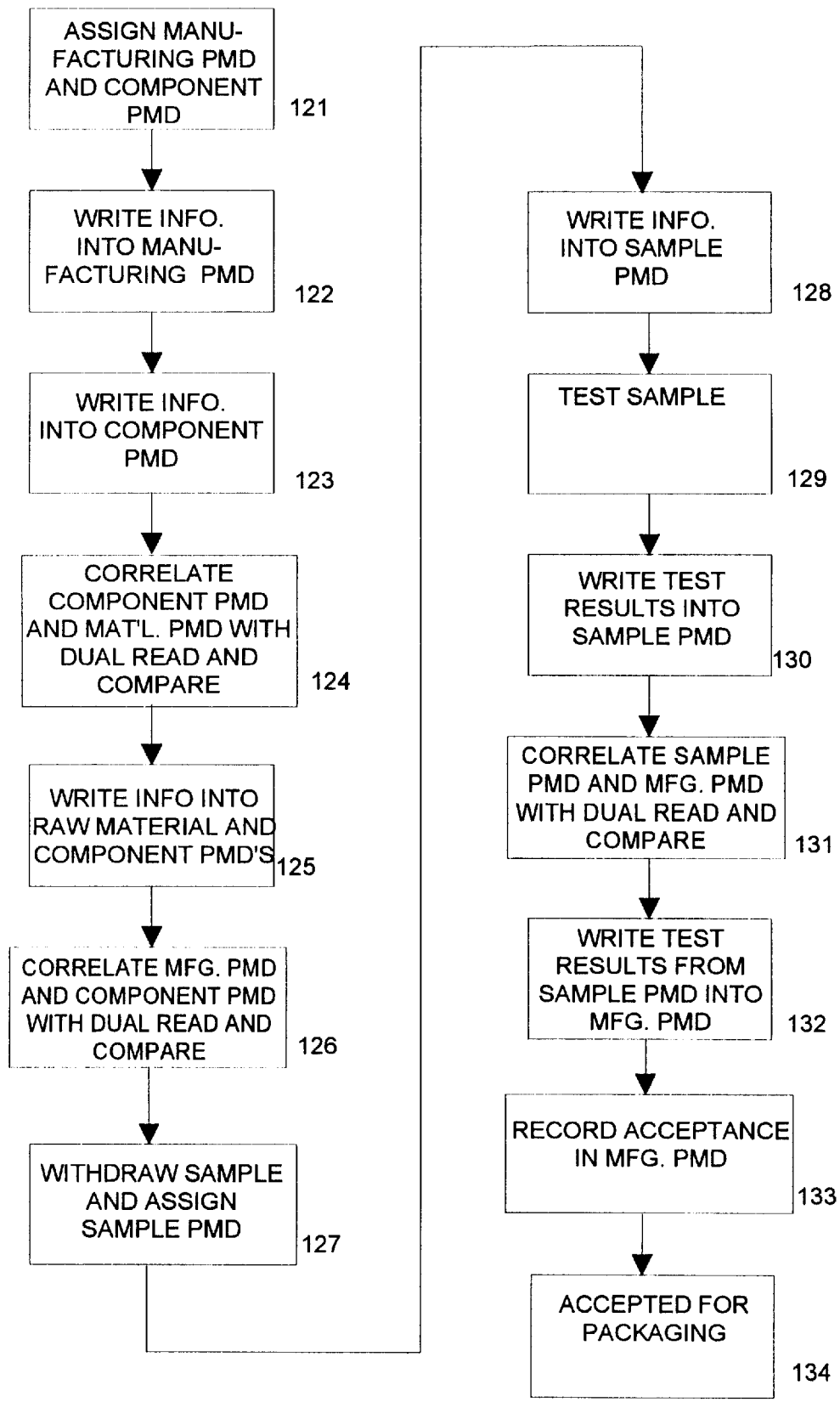
FIG. 3 is a flow chart of a continuation of the flow chart of FIG. 2.
Figure 4:
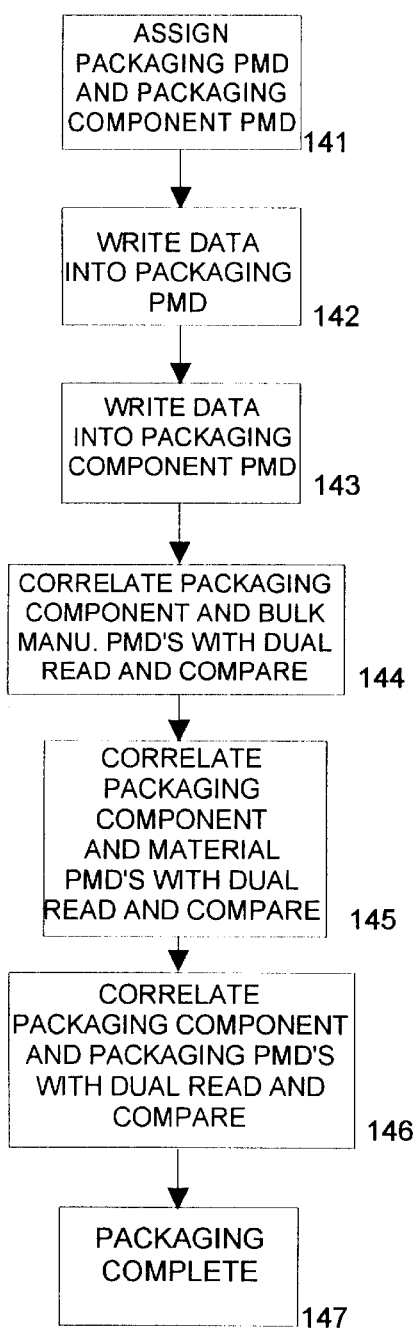
FIG. 4 is a flow chart of a further continuation of the flow chart of FIG. 3.
Figure 5:
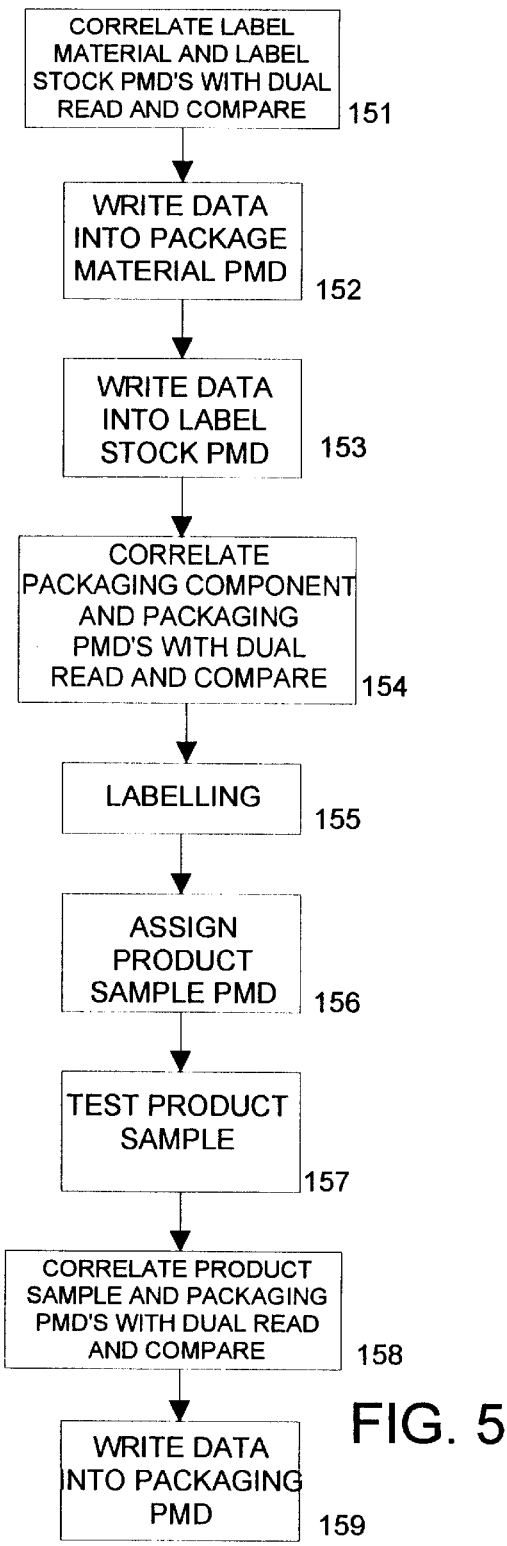
FIG. 5 is a flow chart of a still further continuation of the flow chart of FIG. 3.

Referring now to FIGS. 1–5, a preferred embodiment of the present invention is described with reference to a system for producing pharmaceutical products. It is understood by those skilled in the art that the present invention can be adapted to other processes where high levels of security and preventing the tampering of records is required.

A main processor 15 is connected to a plurality of stations 1–12 via bus 16. Stations 1–12 interact with a plurality of portable memory devices (PMD's) 21–29 by means of electronic signals or electromagnetic waves. The PMD's 21–29, for example, may have up to 1 mb of storage and can be written into and read out from via electronic signals or electromagnetic waves transmitted from stations 1–12 to PMD's 21–29 and received from PMD's 21–29 at stations 1–12 which are stationary or handheld read/write devices. Examples of PMD's and stations are disclosed in U.S. Pat. Nos. 4,242,663, 4,549,264 and 4,724,427, the disclosures of which are hereby incorporated by reference.

The main processor 15 includes a microprocessor and main memory which receives data from stations 1–12 and sends data to stations 1–12 for transmittal to the PMD's 2129. Main processor 15 is preferably a microcomputer having an Intel microprocessor, such as the 80486 or a Macintosh computer based on a Motorola microprocessor.

The first stage of a pharmaceutical manufacturing process involves the reception and acceptance of raw material which is to be used to manufacture a product. When raw material is received at station 1, the name and code of the material, as well as the date, weight or measure and vendor of the raw material is entered into the memory of the main processor 15. At that time in step 101, a raw material PMD 21 is assigned to the lot of raw material and is formatted by main processor 15. The raw material PMD has data written into it from a database in main processor 15 in step 102 via station 1 and this information includes the material name and code, the material lot number, the vendor, the acceptance requirements including the sample required, examination and test required, as well as the criteria for the test, the date received, the total weight or measure and reconciliation limits.

The lot with the raw material PMD 21 is moved into quarantine at station 2 in step 103 whereupon samples are removed for various acceptance tests in step 104. Each sample has a sample PMD 22 assigned to it. Under the control of the main processor 15, data from the raw material PMD is written into the sample PMD's in step 105 including the material name and code, the material lot number, the sample required, the required tests and criteria, the sample date, the I.D. of the person taking the sample.

The samples are moved to station 3 where the tests are conducted in step 106 and each test PMD 22 has data written into it in step 107 reflecting whether or not it passed or failed its particular test, the I.D. of the person making the test and the date of the test.

The sample PMD's 22 are then moved back to station 2 whereupon a dual read and compare is performed in step 108 wherein main processor 15 verifies that common data is read from the sample PMD 22 and the raw material PMD 21 specifically relating to the material name and code and the material and lot number. Upon verification, the data relating to the tests are written from the sample PMD into the raw material PMD in step 109 including the sample date, sampling person I.D., whether the test was passed or not, the test person I.D. and test date.

Based upon the results of the test, the raw material must either be accepted or rejected. This acceptance or rejection is written into the raw material PMD in steps 110 or 111, as well as the identification of the person making the decision. If the material is rejected, it is kept in quarantine or disposed of in step 111. If the material is accepted, the lot of raw material is placed in usable stock.

The manufacturing process uses components of raw materials which have been accepted and placed in usable stock.

In the bulk manufacturing process, initially two PMD's are assigned for a product in step 121. The first PMD is a batch manufacturing PMD 24 and the second PMD is a batch component PMD 23. At station 5, the manufacturing PMD 24 is formatted by the main processor 15 which writes into the manufacturing PMD in step 122, product identification including the product name and code, the strength or dosage of the product, the batch size, the batch lot number and the master production and control for the processing including each step of the production, as well as the process requirements for each step. These requirements include the equipment to be used, the process theoretical yield and acceptable tolerances, and process limitations including tolerances on time, temperature and speed. The in-process test requirements including the number of samples required, the tests required, and their criteria are also recorded.

The component PMD 23 is formatted by main processor 15 which writes into it in step 123 the product identification and master production and control data including for each step, the material required including the active ingredients identified by material name and code and weight or measure required and the same information for any components of the product being manufactured.

When the order is released for production, the date and the electronic signature of the release person is written into the manufacturing PMD and the component PMD.

Component PMD 23 is then moved to station 4 where raw material and raw material PMD 21 are located. A dual read and compare is performed in step 124 between the component PMD and the raw material PMD to verify a common material name and code. Upon verification, the material lot number and the acceptance of the material is read from the raw material PMD and written into the component PMD in step 125. The product identification information is read from the component PMD and written into the raw material PMD. Furthermore, the amount of material dispensed is indicated in the raw material PMD so that a reconciliation can be performed in the main processor 15. The main processor, upon determining that the first raw material has been dispensed, will indicate to an operator that another raw material is needed at station 4, and the steps 124 and 125 will be repeated until all of the required materials have been dispensed.

The component PMD then returns to station 5 for the first step of the manufacturing process. Before the first process step is performed, a dual read and compare operation is performed in step 126 between the component PMD and the manufacturing PMD to verify that common product identification and common master production and control data are contained on the two PMD's.

At this time, various process steps are performed to manufacture the product. For each process step, the dual read and compare operation is performed as further material components are added. Moreover, data is written into the manufacturing PMD for each process step including the fact that material has been dispensed and verified, the equipment that is used, the start time and date, actual yield and whether the yield was within the limits, completion time and whether the completion time was within the limits, the process operator I.D., and the supervisor I.D.

After the process step, the batch is moved to station 6 in step 127 where samples are withdrawn and sample PMD's 25 are provided for each sample. Data is read from the manufacturing PMD and written into the sample PMD in step 128 including product identification, the step number, the sample required, the test required and the criteria.

The tests are performed at station 7 in step 129 and data is written into each sample PMD in step 130 including the sample date, the I.D. of the person taking the sample, whether or not the test was passed, the I.D. of the person administering the test and the date of the test.

The sample PMD is returned to station 6 where a dual read and compare is performed in step 131 with the manufacturing PMD to verify that common data relating to the product identification and the master production and control is present. Upon verification, data relating to the sample and test is read from the sample PMD and written into the manufacturing PMD in step 132. Based upon the test data, the sample is noted as having been completed and accepted and the acceptance and the I.D. of the person making this acceptance is written into the manufacturing PMD in step 133.

The product batch, manufacturing PMD, and component PMD are then moved to station 5 for the next step in the process and steps 124–133 are repeated for each process step.

In the last step of the manufacturing process, the component PMD can be used to obtain capsules for encapsulating the finished product. The component PMD would include for this last step the capsule requirements and the material would be encapsulated at station 5. The same testing can be performed at station 6 and station 7 before the finished bulk product is finally approved and accepted for packaging in step 134.

At this time, the product packaging PMD 26, and packaging component PMD 27, are assigned in step 141. These new PMD's have similar purposes to the manufacturing PMD 24, and the manufacturing component PMD 23, described earlier. The main processor 15 formats the product packaging PMD 26 at station 8 and writes data therein in step 142 including product identification, product name and code, strength and dosage, packaging lot number, package quantity, content quantity, packaging requirements including containers, seals, and labeling requirements, and the final product sampling test requirements. The packaging component PMD 27 is formatted in step 143 with the same product identification information and the specific requirements for packaging materials, labels, and the bulk manufactured product weight or measure. When the packaging process lot is released, this fact is written into the product packaging and packaging component PMD's including the date and electronic signature of the person making the release.

The packaging component PMD 27 moves between stations 8 and 9, as in the case of the manufacturing component PMD which moved between stations 4 and 5, to obtain the accepted bulk product and packaging materials form stock. First, the packaging component PMD 27 is correlated with the bulk manufacturing PMD 24 using the dual read and compare routine at station 9. The manufacturing batch identification is read from the manufacturing PMD and written into the packaging component PMD, and the packaging lot identification is read from the packaging component PMD and written into the manufacturing PMD.

The packaging component PMD 27 is used again in step 145 to correlate with the packaging material PMD 28 at station 9 to verify the correct materials and transfer the identification information between the PMD's. The packaging material PMD is similar to the raw material PMD in function. The packaging components and packaging component PMD return to station 8, and are correlated with the product packaging PMD in step 146 using the dual read and compare routine.

The product is packaged in step 147 and the packaging process parameters are recorded in the product packaging PMD along with the date and packaging person I.D.

After the product is finally packaged in step 147, it must be labeled.

Labels maintained in stock have a label stock PMD 28 associated therewith which includes label identification including product name, strength, dosage form, content quantity and label lot number, whether the labels have been accepted, the date labels were received, the total quantity received and information relating to reconciliation.

The packaging component PMD 27 is used when labels are obtained from the label stock by first doing a dual read and compare with the label stock PMD at station 11 in step 151 to verify the product identification information on both. Upon verification, the label lot number and the fact that the labels were accepted is written into the packaging component PMD 27 in step 152 from the label stock PMD in station 11. Moreover, the quantity of labels dispensed and the I.D. of the person doing the dispensing is written into the packaging material PMD.

The information in the packaging component PMD 27 relating to the batch number of the product and the quantity of labels dispensed is read from the packaging component PMD and written into the label stock PMD in step 153.

The labels and the packaging component PMD 27 return to station 10 and are correlated with the product packaging PMD 26 using the dual read and compare routine. The labeling is performed in step 155 and the product packaging PMD is updated with the identification of the labeling person and the labeling meet the requirements thereof. The packaging component PMD is annotated with the returned and destroyed labels. The returned labels and the packaging component PMD move back to station 11 to update the label stock PMD with the returned and destroyed label data to provide for positive label stock reconciliation.

After the labeling is completed, in step 156 a product sample PMD 29 is formatted by writing the product identification, sample quantity required and the required tests from the product packaging PMD. The product sample PMD travels with the product sample which is thereafter tested at station 12 in step 157 and returned to station 10 where a dual read and compare is performed in step 158 to verify the product identification codes on the product sample PMD and the product packaging PMD. The product inspection data which was written into the product sample PMD during inspection, is then written from the product sample PMD into the product packaging PMD in step 159.

For each recording of data into the PMD's described above, there is preferably a later transfer of that data from the PMD into the main processor 15.

Figure 6:
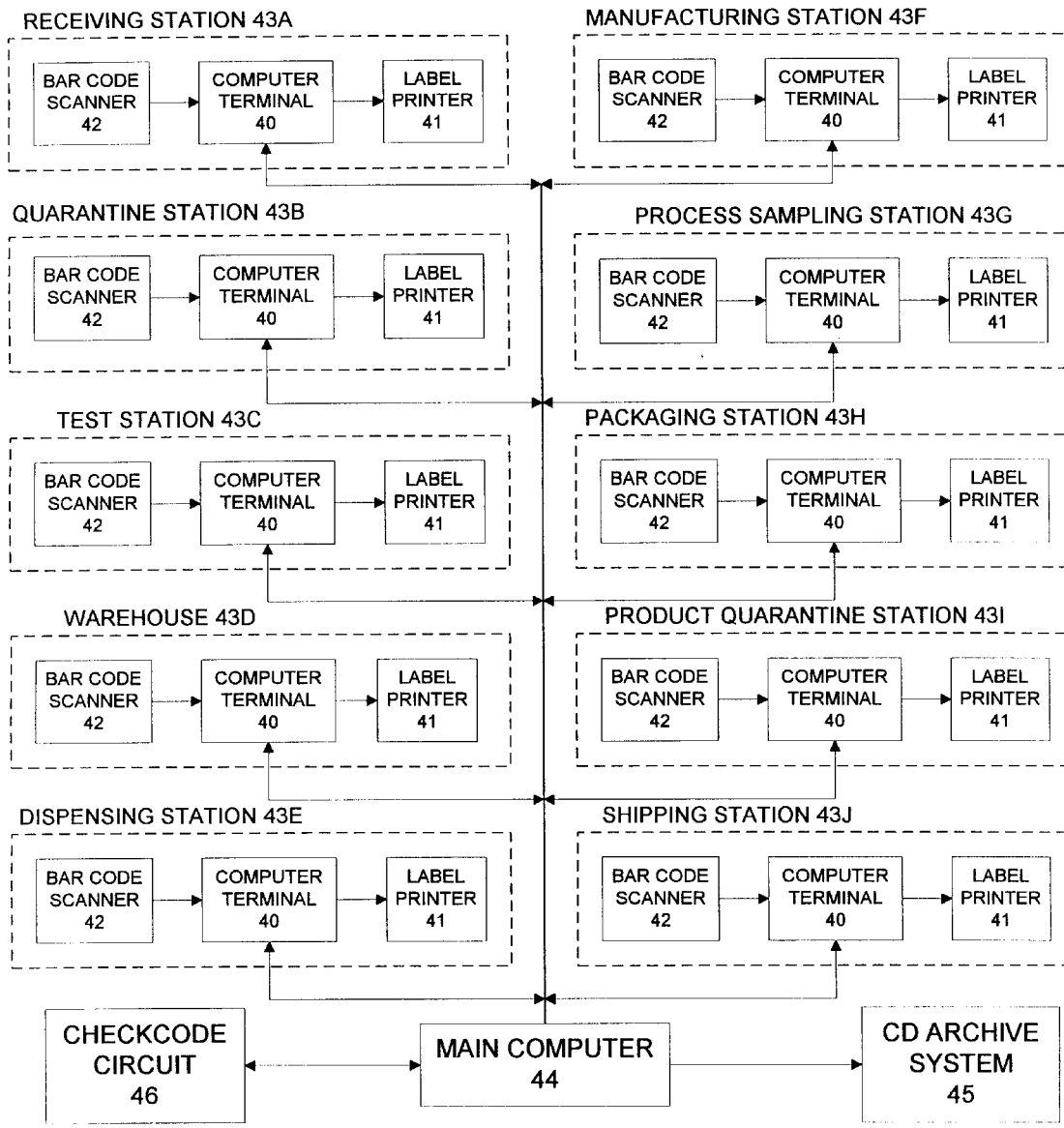
FIG. 6 is a block diagram of another embodiment of the system according to the present invention.

In accordance with the invention shown in FIG. 6, each receiving station includes a computer terminal 40, a bar code label printer 41 controlled by the terminal and a bar code scanner 42 which inputs data into the terminal.

In one embodiment of the present invention, the system includes a receiving station 43A, a quarantine station 43B, a test station 43C, a warehouse storage area 43D, a dispensing station 43E, a manufacturing station 43F, process sampling station 43G, a packaging station 43H, a product quarantine station 43I and a shipping station 43J. All of the stations are connected via a bus to main computer 44 which is connected to a compact disk archiving system 45 and a checkcode circuit 46.

Each entry made at each computer terminal 40 is only permitted after an operator enters an electronic signature which includes a name code or bar code identifying the operator and a password. This information, along with a time and date stamp from the computer terminal, is sent over the bus to the main computer 44. All data to be stored in main computer 44 is first applied to the checkcode circuit which generates a word to be stored along with the data which is representative of the data, the time and date that the data was sent to the main computer for storage and the electronic signature of the operator. In one embodiment of the present invention, the check code generator generates a first group of encrypted data bits corresponding to the operator and unique to that operator, a second group of encrypted data bits representative of the time and date and a third group of bits corresponding to a check sum of the digits of the data. This word is stored in memory with the data itself. Any attempt by a person to change the data in the data word would result in an error being detected. Moreover, any change to the check code would enable the system to determine that the change was made by an unauthorized person or at a date inconsistent with the operation performed.

Figure 7:
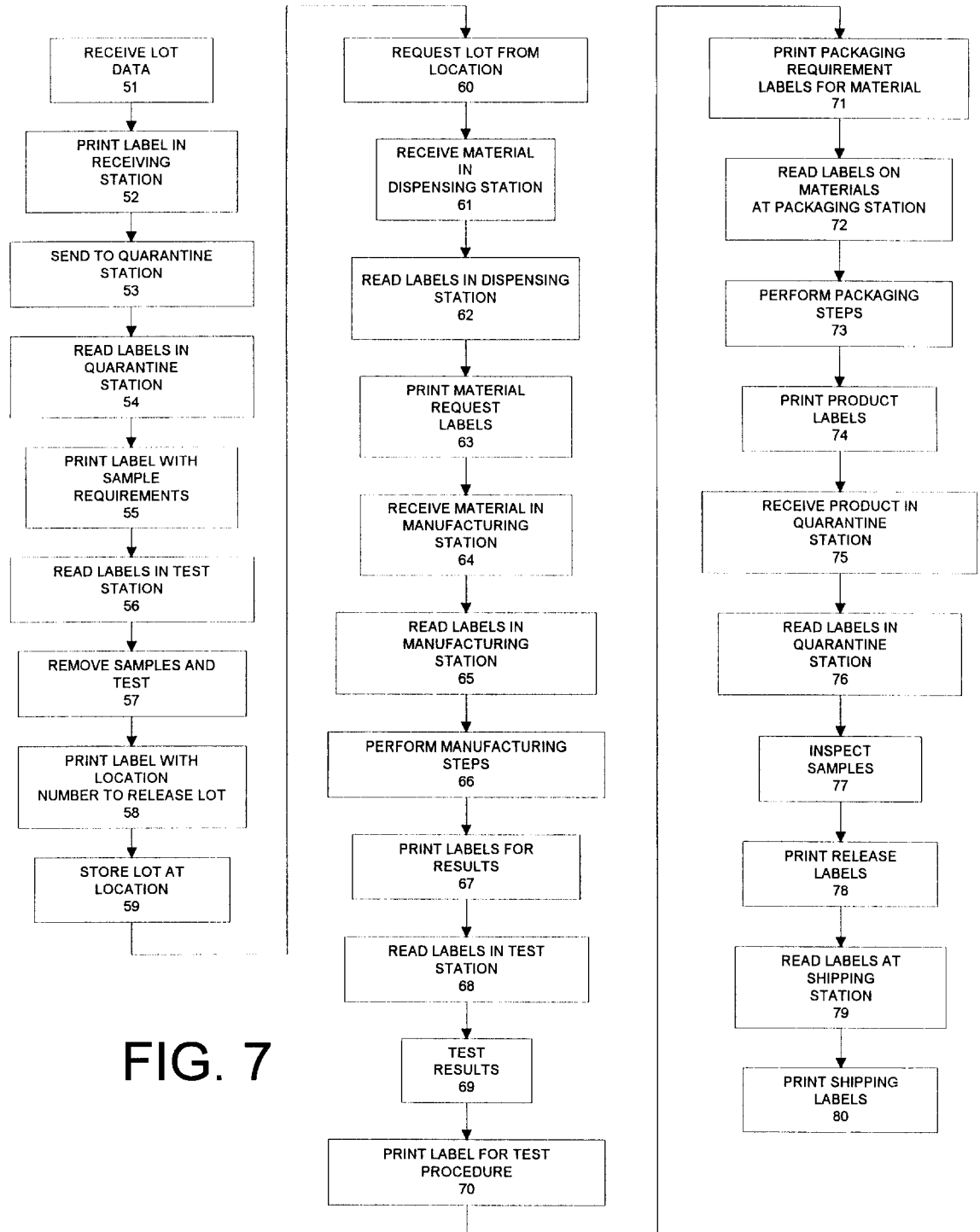
FIG. 7 is a flow chart of a method in using the system of FIG. 6.

In the embodiment of the present invention shown in FIG. 7, lot data is received in step 51 and a bar code label is printed in receiving station 43A in step 52. The lot is then sent to quarantine station 43B in step 54 and a bar code label is printed with the sample requirements in step 55. The labels on the lot are read in step 56 in test station 43C wherein samples are removed and tested in step 57. A bar code label with the location number to release the lot is generated in step 58 and the lot is then stored in warehouse 43D in step 59.

When a lot is requested from a location in the warehouse in step 60, the material is received in a dispensing station 43E in step 61. At that time, the labels on the material are read in step 62 and material request bar code labels are printed in step 63. The materials are received in a manufacturing station 43F in step 64 and labels are read in step 65. The manufacturing steps are performed in step 66 and bar code labels corresponding to the results of those steps are printed in step 67 and applied to the materials.

The labels are read in test or sampling station 43G in step 68 and the test results are reported in step 69 with a bar code label printed for the test procedure in step 70.

The tested material then has packaging requirement bar code labels printed in step 71 and these labels on the materials are read at packaging station 43H in step 72 wherein packaging steps 73 are performed. Product bar code labels are printed in step 74 and the product is received in a quarantine station 43l in step 75. The labels are read in the quarantine station in step 76 and samples are inspected in step 77 and release bar code labels are printed in step 78. The labels are then read at shipping station 43j in step 79 and shipping labels are printed in step 80.

Along the way the data for each of the bar code labels is stored in main computer 44 and thereafter archived on a computer disk in the CD archive system 45 after having the checkcode for each data word generated in the checkcode circuit 46.

It is understood that the embodiments described hereinabove are merely illustrative and are not intended to limit the scope of the invention. It is realized that various changes, alterations, rearrangements and modifications can be made by those skilled in the art without substantially departing from the spirit and scope of the present invention.

What is claimed is:

1. A method for recordkeeping, comprising the steps of:

receiving material to be processed and assigning a machine readable first data record holder to the material to be processed, including a first data record comprising information identifying the material;

reading the first data record holder at a quarantine station;

assigning a machine readable second data record at the quarantine station to samples from the material to be processed including a second data record comprising the electronic signature of an operator taking the samples and information relating to the sample requirements; and reading the second data record holder at the quarantine station;

moving the material to be processed into a processing station and assigning a third data record holder to the material including a third data record comprising the electronic signature of an operator performing a processing operation and information relating to the results of the processing operation; and storing the first, second and third data records in a main data storage device.

2. The method according to claim 1, wherein each step of assigning comprises printing a bar code label and attaching the label to the material.

3. The method according to claim 2, wherein each step of reading comprises scanning a bar code label with a bar code scanner.

4. The method according to claim 1, wherein each step of assigning comprises providing a portable memory device and attaching the device to the material.

5. The method according to claim 1, wherein the second and third data records further comprise a time code.

6. The method according to claim 5, wherein the step of storing comprises generating a checkcode for each data record and storing both in the main storage device.

7. The method according to claim 6, wherein the checkcode is generated by combining data bits relating to the electronic signature, data bits relating to the time code and a checksum of the data record.

* * * * *